(12) United States Patent
Howlett et al.

(10) Patent No.: US 11,266,790 B2
(45) Date of Patent: Mar. 8, 2022

(54) APPARATUS AND METHODS FOR PURGING CATHETER SYSTEMS

(71) Applicant: Becton, Dickinson and Company, Franklin Lakes, NJ (US)

(72) Inventors: Michael W. Howlett, Salt Lake City, UT (US); James V. Mercer, West Jordan, UT (US); Amelio Paolucci, Westminster, CO (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 191 days.

(21) Appl. No.: 16/739,893

(22) Filed: Jan. 10, 2020

(65) Prior Publication Data

US 2020/0147314 A1 May 14, 2020

Related U.S. Application Data

(62) Division of application No. 15/894,477, filed on Feb. 12, 2018, now Pat. No. 10,561,796, which is a
(Continued)

(51) Int. Cl.
*A61M 5/315* (2006.01)
*A61M 5/50* (2006.01)
(Continued)

(52) U.S. Cl.
CPC .... *A61M 5/31595* (2013.01); *A61M 5/31501* (2013.01); *A61M 5/31505* (2013.01);
(Continued)

(58) Field of Classification Search
CPC .......... A61M 5/31595; A61M 5/31505; A61M 2005/31508
See application file for complete search history.

(56) References Cited

U.S. PATENT DOCUMENTS

| 1,393,720 A | 10/1921 | Lomas et al. |
| 2,047,512 A | 7/1936 | Kauffman |

(Continued)

FOREIGN PATENT DOCUMENTS

| AU | 2010247969 B2 | 11/2010 |
| CN | 101119762 A | 2/2008 |

(Continued)

OTHER PUBLICATIONS

Final Office Action in U.S. Appl. No. 12/387,937, dated Apr. 2, 2013, 7 pages.
(Continued)

*Primary Examiner* — Jenna Zhang
(74) *Attorney, Agent, or Firm* — Servilla Whitney LLC

(57) ABSTRACT

Apparatus and methods for providing controlled pressure-flow pulses which purge a catheter system with turbulent flow flushing. Accomplishment of such controlled pressure-flow pulses is provided by a variety of inventive devices including a special plunger rod for a conventional syringe, other interactive parts for conventional syringes, an in-line catheter attachable device which automatically generates the controlled pressure-flow pulses and also single pulse, digitally operated devices.

7 Claims, 9 Drawing Sheets

Related U.S. Application Data division of application No. 14/797,782, filed on Jul. 13, 2015, now Pat. No. 9,889,289, which is a division of application No. 12/387,937, filed on May 9, 2009, now abandoned.

(60) Provisional application No. 61/192,827, filed on Sep. 23, 2008.

(51) Int. Cl.
| | |
|---|---|
| *A61M 5/31* | (2006.01) |
| *A61M 39/22* | (2006.01) |
| *A61M 5/142* | (2006.01) |
| *A61M 25/00* | (2006.01) |
| *A61M 39/24* | (2006.01) |
| *A61M 5/14* | (2006.01) |

(52) U.S. Cl.
CPC ........ *A61M 5/31511* (2013.01); *A61M 5/502* (2013.01); *A61M 5/1424* (2013.01); *A61M 25/00* (2013.01); *A61M 39/22* (2013.01); *A61M 39/225* (2013.01); *A61M 39/24* (2013.01); *A61M 2005/1403* (2013.01); *A61M 2005/3128* (2013.01); *A61M 2005/31508* (2013.01); *A61M 2025/0019* (2013.01); *A61M 2039/242* (2013.01); *A61M 2205/071* (2013.01); *A61M 2206/10* (2013.01)

(56) References Cited

U.S. PATENT DOCUMENTS

| | | | |
|---|---|---|---|
| 3,515,130 A | 6/1970 | Tsujino | |
| 3,769,976 A | 11/1973 | Victory | |
| 3,934,586 A * | 1/1976 | Easton | A61M 5/31595 604/208 |
| 4,210,178 A | 7/1980 | Morse et al. | |
| 4,341,224 A | 7/1982 | Stevens | |
| 4,497,468 A | 2/1985 | Hubbard et al. | |
| 4,596,558 A | 6/1986 | Smith et al. | |
| 4,642,102 A | 2/1987 | Ohmori | |
| 4,650,468 A | 3/1987 | Jennings, Jr. | |
| 4,857,056 A | 8/1989 | Talonn | |
| 4,872,579 A | 10/1989 | Palmer | |
| 4,934,371 A | 6/1990 | Malis et al. | |
| 4,995,869 A | 2/1991 | McCarthy et al. | |
| 5,024,661 A | 6/1991 | Wender et al. | |
| 5,024,681 A | 6/1991 | Chang | |
| 5,059,181 A | 10/1991 | Agran | |
| 5,084,017 A | 1/1992 | Maffetone et al. | |
| 5,171,230 A | 12/1992 | Eland et al. | |
| 5,209,746 A | 5/1993 | Balaban et al. | |
| 5,250,030 A | 10/1993 | Corsich et al. | |
| 5,318,544 A | 6/1994 | Drypen et al. | |
| 5,328,476 A | 7/1994 | Bidwell | |
| 5,350,365 A | 9/1994 | De Godoy Moreira | |
| 5,356,379 A | 10/1994 | Vaillancourt | |
| 5,385,558 A * | 1/1995 | Cottone, Sr. | A61M 5/31555 604/208 |
| 5,514,110 A | 5/1996 | Teh | |
| 5,531,691 A | 7/1996 | Shonfeld et al. | |
| 5,685,864 A | 11/1997 | Shanley et al. | |
| 5,833,669 A * | 11/1998 | Wyrick | A61M 5/31591 604/234 |
| 5,891,052 A | 4/1999 | Simmons | |
| 5,891,062 A | 4/1999 | Schock et al. | |
| 5,975,355 A * | 11/1999 | Cecala | A61M 5/31591 222/283 |
| 6,102,896 A | 8/2000 | Roser | |
| 6,221,045 B1 | 4/2001 | Duchon et al. | |
| 6,283,941 B1 | 9/2001 | Schoenfeld et al. | |
| 6,488,651 B1 | 12/2002 | Morris et al. | |
| 6,500,156 B1 | 12/2002 | Stansbury | |
| 6,579,269 B1 | 6/2003 | Kleyman et al. | |
| 6,620,121 B1 | 9/2003 | McCotter | |
| 6,790,197 B2 | 9/2004 | Kosinski et al. | |
| 6,830,563 B1 | 12/2004 | Singer | |
| 9,517,328 B2 | 12/2016 | Mellejor et al. | |
| 2002/0007143 A1 | 1/2002 | Gordon | |
| 2004/0082920 A1 | 4/2004 | Mori et al. | |
| 2004/0186427 A1 | 9/2004 | Pok | |
| 2005/0004530 A1 | 1/2005 | Grabenkort et al. | |
| 2005/0230575 A1 | 10/2005 | Zelenski et al. | |
| 2006/0241631 A1 | 10/2006 | Kilburn et al. | |
| 2006/0264995 A1 | 11/2006 | Fanton et al. | |
| 2007/0161970 A1 | 7/2007 | Spohn et al. | |
| 2008/0058720 A1 | 3/2008 | Spohn et al. | |
| 2008/0140007 A1 | 6/2008 | Glynn | |
| 2008/0281274 A1 * | 11/2008 | Rolla | A61M 5/288 604/200 |
| 2008/0291274 A1 * | 11/2008 | Merkel | G08B 13/19689 348/143 |
| 2009/0287161 A1 | 11/2009 | Traub et al. | |
| 2010/0076370 A1 | 3/2010 | Howlett et al. | |
| 2015/0314074 A1 | 11/2015 | Howlett | |

FOREIGN PATENT DOCUMENTS

| | | |
|---|---|---|
| CN | 100482290 C | 4/2009 |
| DE | 202005004079 | 7/2006 |
| EP | 0062974 A1 | 10/1982 |
| EP | 2427232 | 3/2012 |
| JP | 08-504352 A | 5/1996 |
| JP | 2004504895 | 2/2004 |
| JP | 2005515847 A | 6/2005 |
| JP | 2008539843 A | 11/2008 |
| JP | 5661747 B2 | 1/2015 |
| JP | 2015042360 | 3/2015 |
| KR | 20040031198 A | 4/2004 |
| TW | 320053 | 11/1997 |
| TW | I679042 B | 12/2019 |
| WO | 0209804 | 2/2002 |
| WO | 2005/074520 | 8/2005 |
| WO | 2010/132290 A3 | 11/2010 |
| WO | 2010132290 A2 | 11/2010 |

OTHER PUBLICATIONS

Final Office Action in U.S. Appl. No. 12/387,937, dated Feb. 18, 2015, 10 pages.
Final Office Action in U.S. Appl. No. 12/387,937, dated Feb. 6, 2014, 8 pages.
Final Office Action in U.S. Appl. No. 12/387,937, dated Jun. 23, 2011, 7 pages.
Non-Final Office Action in U.S. Appl. No. 12/387,937, dated Dec. 12, 2012, 7 pages.
Non-Final Office Action in U.S. Appl. No. 12/387,937, dated Feb. 3, 2011, 10 pages.
Non-Final Office Action in U.S. Appl. No. 12/387,937, dated Oct. 7, 2013, 7 pages.
Non-Final Office Action in U.S. Appl. No. 12/387,937, dated Sep. 17, 2014, 9 pages.
PCT International Preliminary Report on Patentability on PCT/US2010/033999, dated Nov. 9, 2011, 14 pages.
PCT International Search Report in PCT/US2010/033999, dated Nov. 4, 2010, 6 pgs.
PCT International Written Opinion in PCT/US2010/033999, dated Nov. 4, 2010, 13 pages.

* cited by examiner

# APPARATUS AND METHODS FOR PURGING CATHETER SYSTEMS

CROSS-REFERENCE TO RELATED APPLICATIONS

This Application is a divisional of U.S. patent application Ser. No. 15/894,477, filed Feb. 12, 2018, now U.S. Pat. No. 10,561,796 issued on Feb. 18, 2020, which is a divisional of U.S. patent application Ser. No. 14/797,782 filed Jul. 13, 2015, now U.S. Pat. No. 9,889,289, which is a divisional of U.S. patent application Ser. No. 12/387,937 filed May 9, 2009, which claims the benefit of priority from provisional U.S. Patent Application No. 61/192,827 filed Sep. 23, 2008, titled TURBULENT FLOW SYRINGE AND FLUID PATHWAY INSERT, the disclosures of which are hereby incorporated by reference in their entirety.

FIELD OF INVENTION

This invention is associated with apparatus and methods for clearing catheter systems (e.g. IV lines) by creating controlled and consistent turbulent flushing pressure and flow within the system to purge the line of unwanted residue, and, in particular, the invention is associated with apparatus and methods for creating such turbulent flushing pressure and flow substantially independent of clinician technique.

BACKGROUND AND RELATED ART

It is well known in IV care art that turbulent "start-stop" or "push-pause" flushing of IV catheters, e.g. central venous catheters, has become an accepted method for purging matter from catheters and, thereby, preventing build-up of deposits of blood, blood residue and IV drugs within a catheter. Such build-up can cause partial or complete blockage of the fluid pathway in a catheter system, requiring expensive and potentially dangerous methods for purging the catheter or necessitating a total catheter exchange. Often, such blockages lead to interruptions in therapy (e.g. IV therapy) that may compromise patient care. Further, build-up of residue within a catheter can also increase infection risk by providing a breeding medium for microorganisms. For this reason, push-pause flushing is traditionally, and more or less universally, taught to healthcare workers.

Push-pause (or turbulent) flushing simply requires a clinician to alternately increase and decrease an associated infusion rate during flushing. However, efficiency and success of catheter purging using push-pause flushing is well known to be completely dependent upon individual awareness, compliance and technique and a successful purging operation is often incomplete and problematic. For this reason, many users may not use such turbulent flushing effectively while others, due to lack of knowledge or perception of value, may not use it at all.

Also, other than using turbulence for catheter clearance, syringes, pumps and other fluid forcing mechanisms associated with IV infusion are substantially operated in a laminar flow domain. When pulsatile flow is used, pressure and flow characteristics are constrained well below those turbulent and volumetric flow levels required for effective catheter purging.

In the wide spectrum of syringe design, it is common to find art which provides periodic stops of various types and kinds for syringe plungers. Generally, many such stops are employed to aid in accurately measuring and dispensing a portion of a syringe fill. Once such stops are reached, it is common for the plunger to be released to thereby permit controlled and substantially laminar flow to the next stop. In other words, such stops are generally released without a calculated, intentional force to propel the stopper with sufficient force for catheter purging. Other stops are commonly used to limit a syringe to a single use. Generally, these stops are hard and cannot be reasonably overcome, as is common in single-use hypodermic syringes.

An example of a plunger stop for the purpose of limiting injection of fluid from a syringe is found in U.S. Pat. No. 4,642,102 issued Feb. 10, 1987 to Hirofumi Ohmori (Ohmori). Ohmori discloses stops which engage recesses in a plunger rod associated with a plunger to interrupt discharge from the syringe. After each stop, the plunger rod is strictly stopped such that no excessive force is able to drive the plunger rod further. Similarly U.S. Pat. No. 5,024,661 issued Jun. 18, 1991 to Harry Wender (Wender) discloses a single use syringe having recesses along a plunger rod.

U.S. Pat. No. 5,318,544 issued Jun. 7, 1994 to John Drypen, et al. discloses a metering syringe having a plunger rod containing a plurality of stop surfaces. The stop surfaces are spaced apart to define a predetermined dose volume. Plunger rod rotation relieves each stop to permit further dispensing.

U.S. Pat. No. 5,059,181 issued Oct. 22, 1991 to Robert B. Agran (Agran) also discloses a syringe assembly having recesses in a plunger rod which are used to retard a second rearward displacement of the plunger rod associated with a second use of the syringe assembly. In similar manner, U.S. Pat. No. 5,084,017 issued Jan. 28, 1992 to John Maffetone (Maffetone) discloses a single use syringe having a notched plunger rod. The syringe of Maffatone is taught to operate smoothly, but to dissemble itself at the completion of a single use cycle.

U.S. Pat. No. 5,280,030 issued Oct. 5, 1993 to Cesar G. Corsich, et al. (Corsich) discloses a hypodermic syringe having a blockable piston capable of preventing recharge and reuse under some conditions.

U.S. Pat. No. 5,328,476 issued Jul. 12, 1994 to James Bidwell (Bidwell) discloses a single-use hypodermic syringe apparatus. Rachet grooves in an associated plunger rod are used as lock members such that when plunger is fully inserted or reinserted into a casing, the plunger is prevented from being withdrawn relative to the casing.

U.S. Pat. No. 6,283,941 issued Sep. 4, 2001 to Joel Schoenfeld, et al. (Schoenfeld) discloses a rod-like syringe plunger having a plurality of bead-like rachet teeth. Schoenfeld also discloses a single use syringe. Of particular note is the statement, "It is a further object of the present invention to provide a single use syringe which has a smooth mechanical operation and a plunger retraction force less than the industry maximum standard." Such objectives are commonly held in the syringe art for manipulating syringe plunger rods.

U.S. Pat. No. 5,891,052 issued Apr. 6, 1999 to Paul L. Simmons (Simmons) teaches a syringe plunger sabot and sabot lock disposed within a syringe body, the sabot lock mechanism being selectively moveable between a locked and unlocked position. Thereby an engagement is made to create a vacuum for extracting material into the syringe body.

U.S. Pat. No. 6,488,651 issued Dec. 3, 2002 to David Paul Morris et al. (Morris) discloses a mixing syringe having a plunger rod dasher which permits flow within the barrel for communicating material to be mixed with material in a more proximal chamber. Other cylindrical barriers provide within chamber defining spaces which are selectively displaced by movement of the plunger rod. Other than resistances of fluid dynamics and friction (and stiction), no other retarding forces are taught.

U.S. Pat. No. 6,579,269 BI issued Jun. 17, 2003 to Gennady I. Kleyman (Kleyman) discloses a dose measuring syringe. A plunger rod, as taught in Kleyman, has formations which increase resistance to displacement of the plunger rod and to produce an audible sound corresponding to a predetermined volume for a measured dose. Even so, there are no teachings in Kleyman for providing momentary stops which produce a predetermined amount of turbulent flow in a catheter.

U.S. Pat. No. 5,685,864 issued Nov. 11, 1997 to Laurence M. Shanley, et al. (Shanley) discloses an aspiration syringe device which operates oppositely to aspirate rather than discharge into a connected site. A right angle stem of an associated plunger is equipped with spaced flanges. Interior of the syringe barrel is equipped with at least one stop. When a flange is contiguous with a stop, advancement of the plunger is prohibited. Rotation of the plunger permits further advancement.

U.S. Pat. No. 4,995,869 issued Feb. 16, 1991 to Martin McCarthy (McCarthy) discloses a single-use hypodermic syringe. A syringe barrel according to McCarthy has an interior undulating surface over which a skirt rides rearward under direction of a proximally directed manual force. While it seems apparent that the undulations will cause a pulsation in flow while discharging fluids via a patient needle, it is clear that there are no related teachings for creating turbulent flow in a catheter, a subject untouched in McCarthy.

Generally, in summary, prior art, of which art cited above is an example, discloses and teaches plunger rod having slots, grooves and rachet teeth are for providing obstructions used for measuring predetermined volumes of dispensed fluids or for stops associated with providing single use syringes. Just as clinician-dependent generation of push-pause flow is problematic, all such art is void of teachings which assure successful creation of turbulent flow for clearing an associated attached catheter system. Such is the specific and precise purpose of the present invention.

BRIEF SUMMARY AND OBJECTS OF THE INVENTION

In brief summary, this novel invention alleviates all of the known problems related to generating controlled and predetermined push-pause pressures and flows thereby providing controlled and consistent turbulent flow which is effective in purging matter disposed within a catheter system. The invention comprises methods and apparatus which are defined and designed to produce pressures resulting from dynamic releases by predetermined forces, each for a period which provides a controlled and consistent surge to effectively produce turbulent purging fluid flow at a site of concern within a catheter system.

Generally, such flow is provided to a catheter system from a source of flush liquid from a container sized to hold a volume of liquid consistent with flow volume requirements of a desired pressure pulse. In each case, an actuator opens a valve mechanism at a predetermined pressure to initiate the desired liquid pulse pressure and resulting liquid flow. The sensing actuator has an operating hysteresis which ultimately stops flow to end the pressure pulse. Of course, an implement which, by example, may be a pump or piston, is a crucial part of the apparatus for providing sufficient pressure to activate the valve mechanism. To retain adequate pressure throughout the pulse, a memory element provides a source of stored energy received from the implement and releases the stored energy upon valve mechanism opening to retain the turbulent flushing fluid pressure and flow for a desired pulse period.

One embodiment of the apparatus is application of the invention to a syringe, and more specifically, to a plunger rod of a syringe. In such a case, the barrel of a syringe is the container. Displacement of the plunger rod (and associated plunger) within the barrel acts as an implement to dispense liquid from the syringe. Commonly found at the proximal end of conventional syringes is a retention ring formed of reduced diameter relative to the diameter of the rest of the syringe barrel. This retention ring is used as a tactile indicator between an entry disk disposed on the stem of a plunger rod just proximal from the plunger affixed to the plunger rod, providing an impedance which must be overcome to extract the plunger rod (and plunger) from the syringe barrel.

At least one actuating geometry, sized and shaped to require a predetermined force to displace the actuating geometry past the retention ring, is disposed proximally on the stem relative to the entry disk. Forcing the actuating geometry past the retention ring yields the force necessary to provide desired turbulent flushing fluid pressure and initiate flow. Such geometry may be a disk on the plunger or an interfacing nub on exterior edges of shafts of a plunger rod. Reflexive motion associated with forcing the actuating disk past the retention disk provides the memory based, stored energy necessary to assure continuation of forced flow thereby providing the pressure pulse. The length of the pressure pulse is determined by either the plunger being displaced to empty the syringe barrel or a second actuating disk disposed proximally on the stem relative to the actuating disk just forced through the retention ring to provide a tactilely determinable stop. Note, that resistance of this stop, relative to reflexive energy applied to displace the syringe plunger rod, provides the hysteresis specified. In this manner, a conventional syringe barrel, in combination with a plunger rod made according to specifications of the instant invention, can provide desired pulse-pause pressure pulses from a syringe substantially independent of a syringe user. It may be preferred to provide a segment of a plunger rod free of actuating geometry to provide a "no-pulse" segment to enable conventional flush technique to check for possible occlusions and to verify blood return.

In another embodiment, the pulse-pause pressure pulse is provided by an in-line apparatus. Source for fluid is from a receptacle having sufficient volume to fill a container from which the pressure pulse is generated, the container being a hollow cylindrical vessel which receives liquid from the receptacle through a one-way valve. Communication for dispensing liquid to the catheter system is through another one-way valve.

The valve mechanism is a plunger, sized and shaped to displace fluid within the vessel through the one-way valve to the catheter system. Further, the vessel has a retention ring similar to the retention ring of the barrel of a conventional syringe. A valve-actuating disk associated with the plunger is sized and shaped to require predetermined force necessary to generate a desired pulse toward the catheter system. Volume of the vessel determines pulse volume. Again, as in the case of the syringe, reflexive action resulting from release of force when the actuating disk is driven past the retention ring assures adequate pulse pressure. The actual implement for driving the plunger is derived from a button affixed to the plunger and associated rod whereby the plunger is manually driven through the vessel. A spring disposed to be compressed when the pressure pulse is generated stores energy to return the plunger and refill the vessel for a subsequent pulse-pause cycle.

Other embodiments of the present invention involve a pressure sensitive switch having an actuator which opens the valve at a higher predetermined pressure and closes at a lower predetermined pressure. Generally, the source is a fluid receptacle upstream from a pressure-providing device which provides fluid dispensed at a predetermined pressure and flow. A vessel acts as a container which communicates with the pressure providing device through a flow restrictor. Further, the vessel communicates with the catheter system through the pressure sensitive valve. The pressure sensitive valve is selected to have an opening pressure which provides a fluid pulse having desired turbulent flow characteristics and closing at a pressure after a desire flow volume has been achieved and pressure within the vessel is reduced below the lower predetermined pressure.

In one of these other embodiments, a pump provides pressure of the source. A spring loaded piston chamber provides opportunity to gather volume for the pressure pulse which fills at a pressure lower than the higher predetermined pressure through a flow restrictor affixed to the output of the pump, but at a pressure higher than the lower predetermined pressure. Thus, the higher predetermined pressure is reached only upon filling the chamber. Once the chamber is filled, the valve is opened by the actuator to initiate the controlled pressure pulse. When the chamber is emptied, pressure in the vessel drops below the lower predetermined pressure and the actuator closes the valve. If this embodiment remains affixed to the catheter system a subsequent pressure pulse is generated automatically.

Another of other embodiments involves a squeezable tube. In this case the tube communicates with the catheter system through a pressure sensitive valve, having valve actuator opening characteristics as disclosed supra. Upstream the tube communicates with the source through a one-way valve. Pressure from the source does not reach or exceed the higher predetermined pressure, but is sufficient to fill the tube. Thus, pressure from the upstream source and elastic memory in the tube cause the tube to fill through the upstream one-way valve. Once the tube is adequately filled, it is selectively squeezed to cause the pressure to rise to at least the higher predetermined pressure. Once pressure within the tube is at or above the higher predetermined pressure, the valve is opened and the pressure pulse is initiated. The pressure pulse is continued by reflexive action following valve opening. Expulsion of liquid from the tube ultimately results in valve closing ending the pressure pulse. The pressure pulse may be continued until the tube is substantially empty.

Methods for using embodiments of the instant invention generally involve filling a chamber or vessel, of predetermined size, from which a pulse of liquid is to be dispensed, causing pressure within the chamber or vessel to exceed a predetermined pressure and selectively opening a pathway to the catheter system only when that pressure is achieved. In that manner, a desired, controlled pulse-pause pressure pulse is achieved and provided substantially independent of performance of a user.

Accordingly, it is a primary object to provide apparatus which provides substantially user independent, controlled pulse-pause pulsatile flow of sufficiently turbulent flushing pressure and flow within a catheter system to substantially purge the line of unwanted residue.

It is a primary object to provide such apparatus which is used within a barrel of a conventional syringe.

It is another primary object to provide such apparatus which provides in-line operation between a fluid source and the catheter system.

It is an object to provide such apparatus which provides for a series of manually generated pulse-pause pressure pulses.

Is a an important object to provide such apparatus which uses a pump as an implement.

It is another object to provide apparatus which provide controlled pressure pulses resulting from opening and closing a pressure sensitive valve.

These and other objects and features of the present invention will be apparent from the detailed description taken with reference to accompanying drawings.

Definitions of Some Terms Used in the Specification catheter system\n: a combination of tubes and other devices used to deliver fluids to patients, e.g. a medical catheter (e.g. IV catheter), delivery tubing (e.g. feeding tube) and associated connectors
fluid\n: a gas or liquid
IV\adj: a mode of delivery of fluids to a patient, in this case the mode is Intravascular laminar flow: streamline flow which is relatively smooth and even, such as flow near a solid boundary and contrasted with turbulent flow
turbulent flow\n: a fluid flow in which the velocity at a given point varies erratically in magnitude and direction with time and is thus essentially variable in pattern and is contrasted with laminar flow
valve mechanism\n a fluid control device generally defined herein to be a device for initiating a pressure pulse when opened and ending the pressure pulse when closed; within this general definition, pulse-pressure generating action of a syringe plunger rod being displaced to actuate a pressure pulse is considered to be a valve mechanism

DETAILED DESCRIPTION OF THE ILLUSTRATED EMBODIMENTS

In this description, the term proximal is used to indicate the segment of the device normally closest to the object of the sentence describing its position. The term distal refers to a site opposite the proximal section. Reference is now made to the embodiments illustrated in FIGS. 1-20 wherein like numerals are used to designate like parts throughout.

Figure 1:
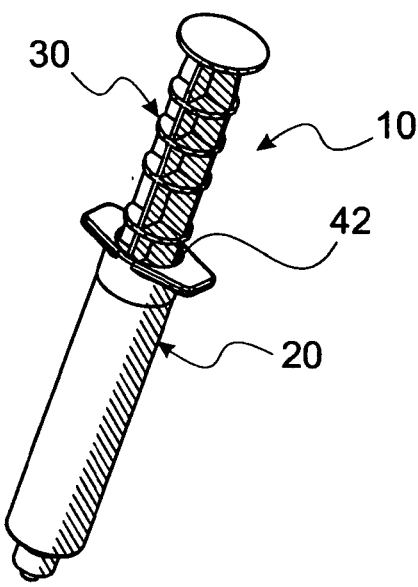
FIG. 1 is a perspective of a syringe and plunger rod made according to the present invention where stem of the plunger rod has a plurality of disks disposed upon the length thereof.

Reference is now made to FIG. 1 wherein a preferred embodiment of a syringe/plunger rod combination 10 of the instant invention is seen. Combination 10 comprises a conventional syringe barrel 20 and a plunger rod 30. Salient features of combination 10 are better seen in FIG. 2 to comprise barrel 20 having a retention ring 40 disposed at proximal barrel hole opening 42 and plunger rod 30 comprising a plurality of actuating geometry, interfaces or rings, generally numbered 50) disposed along a stem 60 thereof. In addition, as is common with plunger rods of conventional syringes, plunger rod 30 has a plunger 70 affixed to the distal end 80 of stem 60. It may be noted that distal end 80 has a threaded geometry portion 90 which permits plunger rod 30 to be affixed to plunger 70 after barrel 20 is filled with liquid, generally referenced as liquid 72. A plunger rod 30 is seen alone in FIG. 3 providing a clearer view of threaded portion 90.

Further, plunger rod 30 has a first ring 92 which can be forced past retention ring 40 when plunger 70 and stem 60 are inserted into barrel 20. First ring 92 is sized and shaped to be forcible displaced through retention ring 40, but provide a tactilely discernable stop such that plunger 70 is not inadvertently displaced out of barrel 20.

Each actuator ring 50 is sized and shaped to be obstructed by retention ring 40. Each actuator ring 50 is further sized and shaped to require a predetermined force which must be exceeded to displace a contacting actuator geometry (e.g. retention ring interface 50) past retention ring 40. For this reason, fluid within barrel 20 is displaced with resulting acceleration and velocity resulting from the predetermined force when the contacting ring 50 is releasably displaced through retention ring 40. Generally the resulting acceleration and velocity is of liquid which is discharged from syringe barrel 20 to turbulently flush liquid 72 through an associated catheter system. In this manner, each time a contacting ring 50 is displaced past retention ring 40 a pulse of pressurized liquid 72 is purged into the catheter system providing a turbulent flushing pulse of liquid 72 there through.

As well, a more proximal ring 94 of rings 50 may be further shaped and sized to require a force which is greater than more distal rings 50 to provide a reminder that the pulse resulting from actuation using ring 94 is the last pulse provided by liquid 72 from combination 10. For this reason, ring 94 may be referenced as reminder ring 94 hereafter. Note, that, if plunger rod 30 is not displaced sufficiently far into barrel 20 to displace reminder ring 94 past retention ring 40, no back flow or reflux should occur in an associated catheter system. Note that proximal end 98 of stem 60 is convex or dome shaped to facilitate application of digital force against plunger rod 30.

As well, it may be noted that rings 50 are not necessarily spaced uniformly. As an example a space 99 between first ring 92 and next most proximal ring 50 is relatively large compared to space between other rings, generally numbered 50. This provides for a "no-pulse" segment which may be used for conventional sampling for catheter blood flow to assure proper catheter operation.

Figure 2:
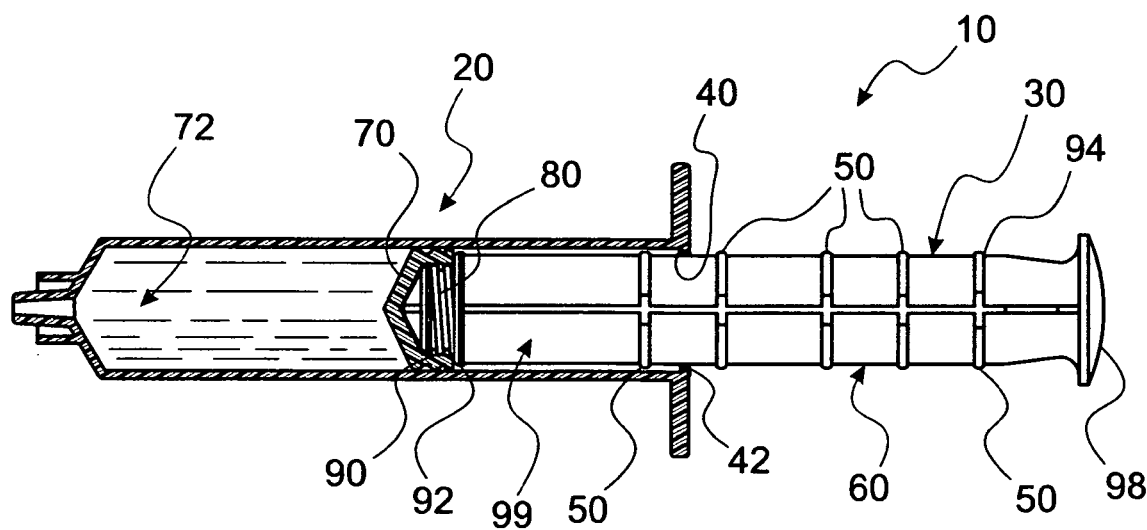
FIG. 2 is a cross section of the syringe and plunger rod and seen in FIG. 1.
Figure 2A:
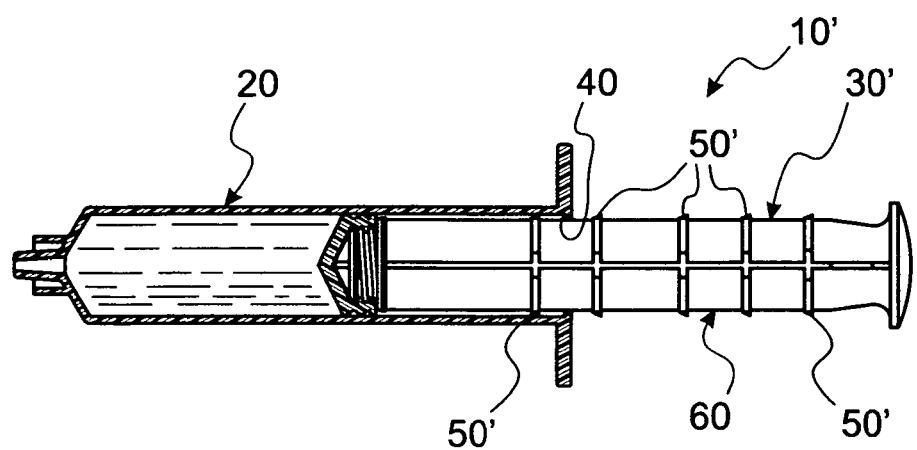
FIG. 2A is a cross section of a syringe and plunger rod which is similar to the syringe and plunger rod of FIG. 2, but wherein edges of disks are shaped to facilitate displacing the plunger rod into the syringe and deterring the plunger rod from being removed from the barrel, once so displaced.

Attention is now directed to FIG. 2A wherein a second combination 20' of a conventional syringe barrel 20 and a plunger rod 30' is seen. Plunger rod 30' is similar to plunger rod 30, having a series of actuator rings 50' disposed along the length thereof. However, in the case of combination 10', rings 50' are shaped and sized (as seen in FIG. 2A) to be more easily displaced into barrel 20 (and distally through retention ring 40) than displaced barrel 20 (proximally through retention ring). Such meets a condition whereby plunger rod 30' is not easily removed from barrel 20, once used to promote a single use application.

Figure 2B:
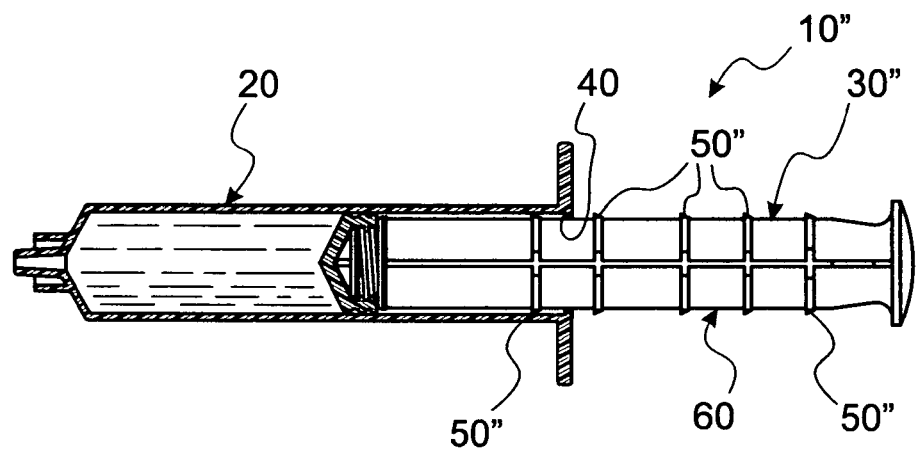
FIG. 2B is a cross section of a syringe and plunger rod which is similar to the syringe and plunger rod of FIG. 2, but wherein edges of disks are shaped to facilitate displacing the plunger rod out of the syringe once displaced therein.

On the other hand, it may be desired to refill and reuse such a combination. In such a case, it is desired to displace a plunger rod 30" of a third combination 10" more easily proximally than distally. In such a case, actuating rings 50'" disposed along a stem 60 are shaped as seen in FIG. 2B.

Figure 2C:
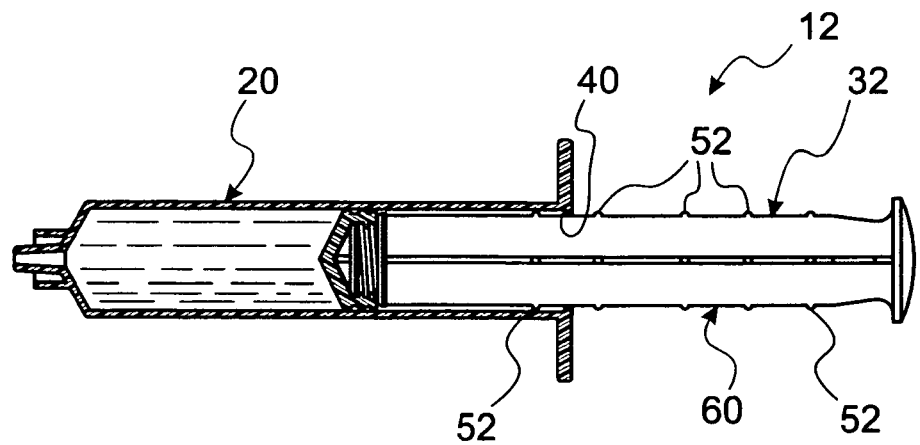
FIG. 2C is a cross section of a syringe and plunger rod which is similar to syringes and plunger rods of FIGS. 2, 2A and 2B, but having nubs along a shaft of a plunger rod instead of disks.
Figure 3:
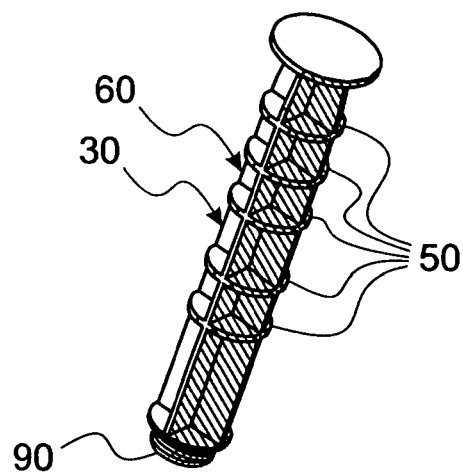
FIG. 3 is a perspective of the plunger rod seen in FIG. 1.

Rings 50 seen in FIG. 2, may be replaced by nubs 52 on a plunger rod 32 as seen as combination 12 in FIG. 2C. Replacement of rings 50 by nubs 52 may be done without degradation of effect of producing desired turbulence by sizing and shaping nubs 52 to require forces similar to that required of rings 50 for displacement past retention ring 40.

Figure 4:
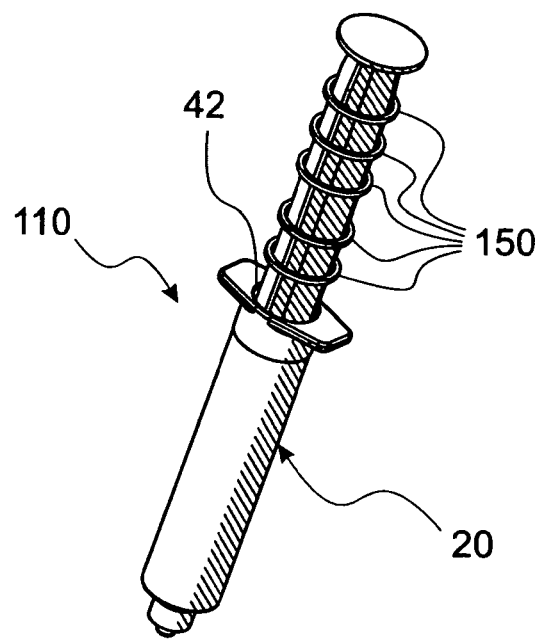
FIG. 4 is a perspective of a syringe and plunger rod wherein the plunger rod is similar to the plunger rod of FIG. 1 but fabricated with a plurality of breakaway rings disposed about to stem of the plunger rod.
Figure 5:
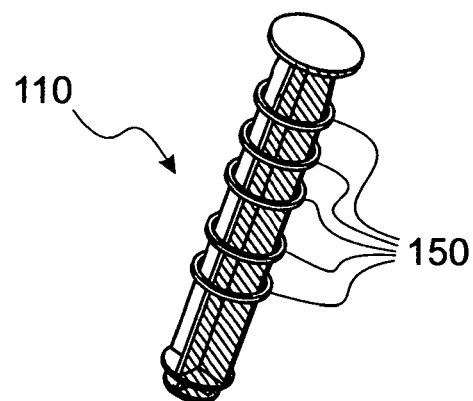
FIG. 5 is a perspective of the plunger rod seen in FIG. 4.
Figure 6:
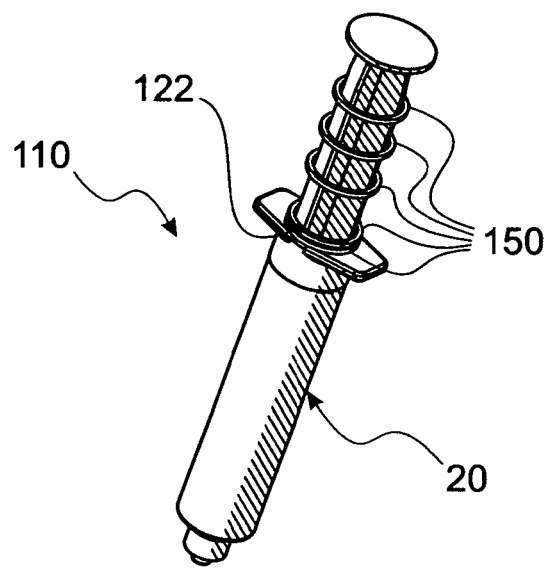
FIG. 6 is a perspective of the syringe and plunger rod seen in FIG. 4 with at least one breakaway ring sheered from the stem of the plunger rod.

Another embodiment, seen as combination 110, of the instant invention is seen in FIGS. 4-6. As in combination 10, combination 110 comprises a conventional syringe barrel 20. Note that syringe barrel 20 has a proximal entry hole 122 associated with retention ring 40. As seen in FIGS. 4 and 5, an associated plunger rod 30 also comprises a series of actuator rings, generally numbered 150. disposed along a stem 60 of plunger rod 130. However, rather than being sized and shaped to be forced through retention ring 40 of barrel 20 to create a desired pressure pulse, rings 150 are affixed to stem 60 in a manner which permits each actuation ring 150 to be sheared from stem 60 as it is displaced into barrel entry hole 42.

Shear force at separate actuation rings 150 from stem 60, similar to displacement force past retention ring 40 of combination 10, is geometrically and mechanically designed to provide a predetermined acceleration and velocity which purveys desired turbulent flow to purge and discharge unwanted contaminants from a downstream catheter system. Note, in FIG. 6, that a first more distally disposed actuator ring 150 is seen to be captured by a second, more proximally disposed actuator ring 150 exterior to hole in FIG. 6. Note that piling up of sheared actuation rings 150 may be used to prevent a syringe from being fully evacuated.

Figure 7:
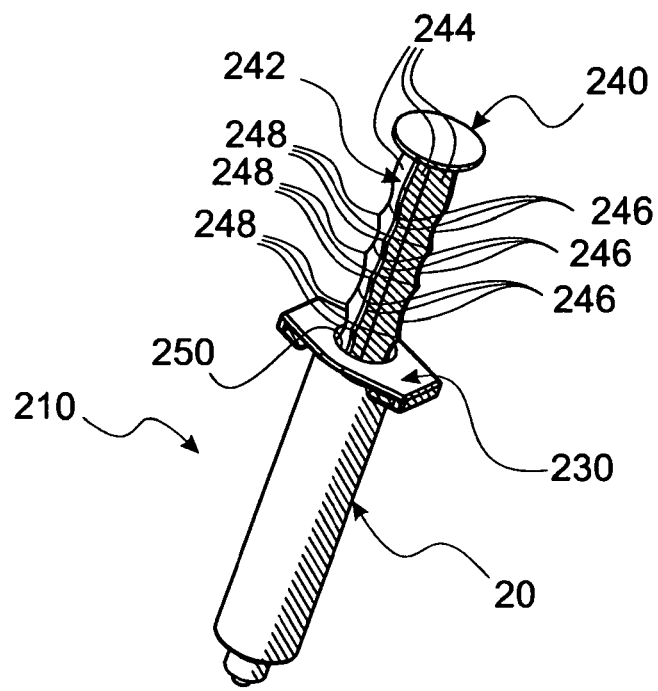
FIG. 7 is a perspective of a syringe and plunger rod wherein the plunger rod is similar to the plunger rod of FIG. 1 but having a pattern of undulations on the stem and a constraining elastomeric ring about the proximal syringe barrel opening.
Figure 8:
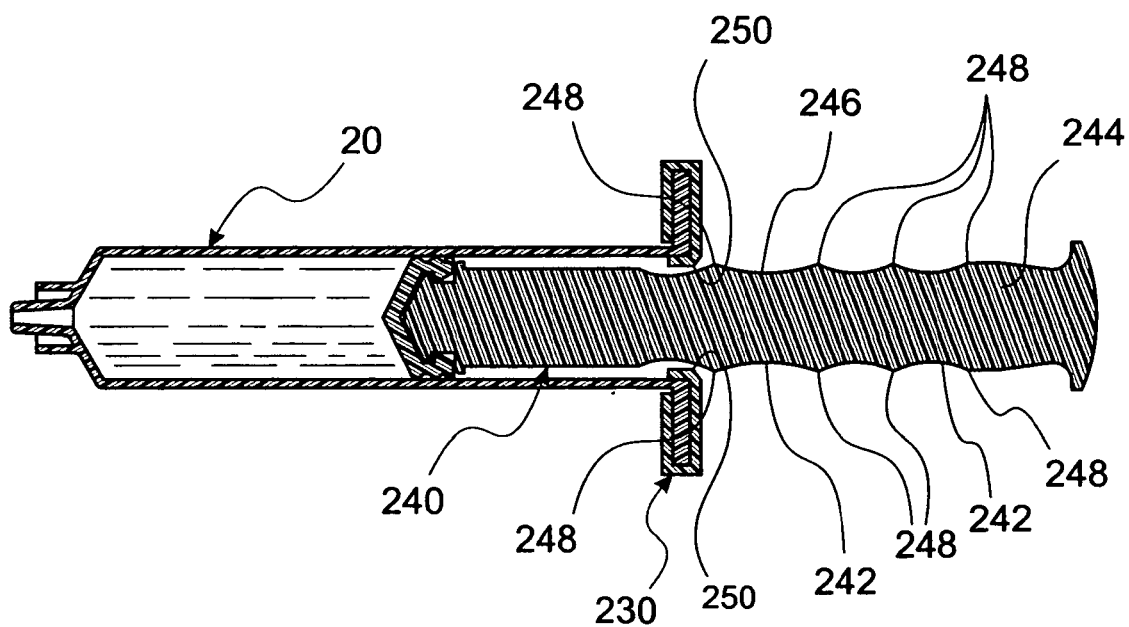
FIG. 8 is a cross section of the syringe, plunger rod and elastomeric ring seen in FIG. 7.

Yet another embodiment of the instant invention is seen as combination 210, which may use a conventional syringe barrel 20, is seen in FIGS. 7 and 8. In addition to barrel 20, combination 210 comprises an elastomeric restrictor 230 a plunger rod 240 with a stem 242. Stem 242 comprises a plurality of elongated side members, each numbered 244. Each side member has an undulating exterior edge, numbered 246. High points of the undulations are generally numbered 248.

Restrictor 230 is shaped and configured to provide a port about barrel entry hole 42 (see FIGS. 1 and 2). A restrictor entry hole 250 is sized and shaped to obstruct inward displacement of plunger rod 240 upon collision between restrictor 230 and each high point 248. A combination of selected durometer of the elastomer of restrictor 230, and collision geometry of high points 248 and hole 250 combine to require a predetermined force for further displacement of plunger rod 240. This predetermined force is comparable to the force required for displacement of plunger rod 30 past retention ring 40 (see FIGS. 1-3). In this manner, a pressure pulse which provides turbulent flow for purging an attached catheter system is generated each time high points 248 are displaced through hole 250 of restrictor 230.

Figure 9:
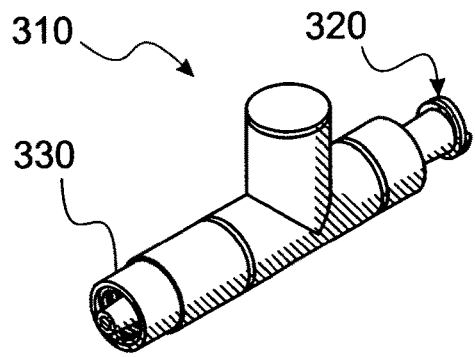
FIG. 9 is a perspective of an automatic, in-line pulsing device made according to the present invention.

Reference is now made to FIGS. 9-12 wherein an in-line automatic pulsing device 310 made according to the instant invention is seen. As seen in FIG. 9, device 310 comprises an upstream or proximal connection 320, into which liquid from a liquid source is provided. Further device 310 comprises an output port and connector 330 which may be connected to a downstream catheter system. For proper operation, liquid pressure available from the source must be greater than desired pressure of a purging liquid pulse emitted by device 310.

Figure 10:
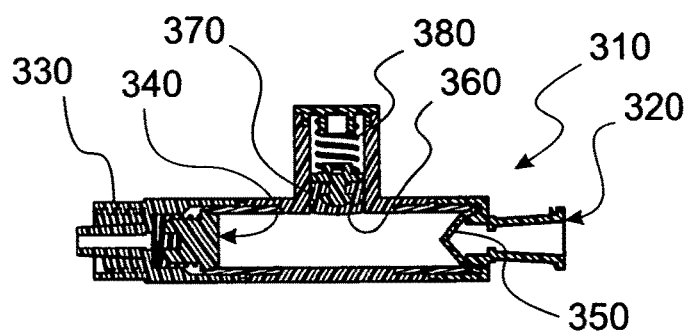
FIG. 10 is a cross section of the automatic, in-line pulsing device seen in FIG. 9 showing state of the device at the end of a pulse.

As seen in FIG. 10, a pressure sensitive valve 340 is disposed to close output port and connector 330 when pressure is below the desired pressure. Just distal from proximal connection 320 is a check valve 350 to obstruct backflow and retard inflow to a predetermined level of flow. Medially disposed between pressure sensitive valve 340 and check valve 350 is a pulse reservoir chamber 360. Disposed within chamber 360 is a piston 370 and spring 380 which acts within chamber 360 to store a volume of liquid when valve 330 is closed.

When choosing pressure sensitive valve 340, a valve should be selected which has an opening pressure to closing pressure hysteresis having a predetermined pressure differential for purposes clarified hereafter. The pressure differential being defined as a difference between release high pressure and a low closing pressure. The high pressure being a pressure which creates a pressure pulse having sufficient force and flow to cause down stream turbulence which purges a desired amount of material from an attached catheter system. The lower pressure being a pressure to which pressure inside device 310 falls after clearing of liquid from chamber 360. Note that, for pressure inside 310 to fall to the lower pressure, inflow from the source must be restricted to a lower flow rate than outflow through output port and connector 330.

Figure 11:
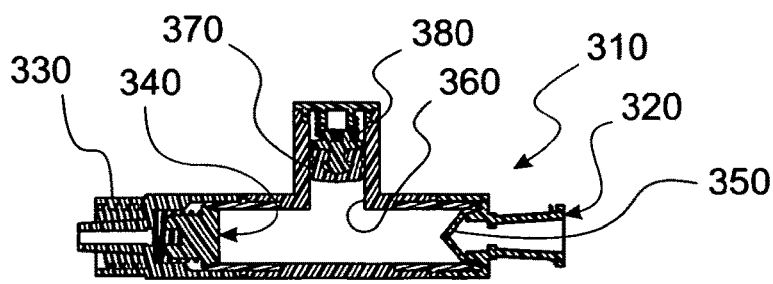
FIG. 11 is a cross section of the automatic pulsing device seen in FIG. 9 showing state of the device when charged before actuating a pulse.
Figure 12:
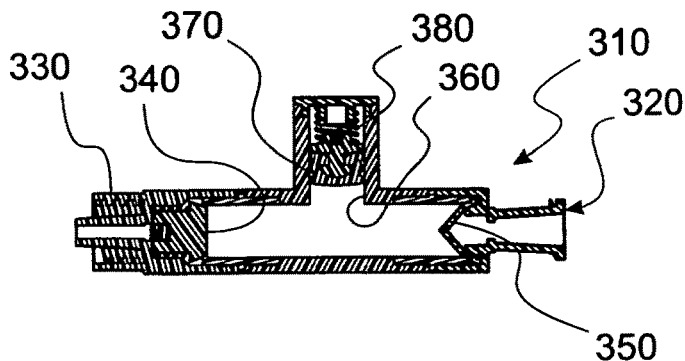
FIG. 12 is a cross section of the automatic pulsing device seen in FIG. 9 showing state of the device during pulse generation.

Steps of operation of device 310 are seen to embody a beginning state seen in FIG. 10 where chamber 360 is empty and spring 380 is decompressed and valve 350 is closed. Subsequent filling of chamber 360 is seen in FIG. 11. Valve 340 is opened when spring 380 is fully compressed to discharge liquid from device 310 thereby. Of course, once valve 350 closes, the pulse cycle repeats.

Figure 13:
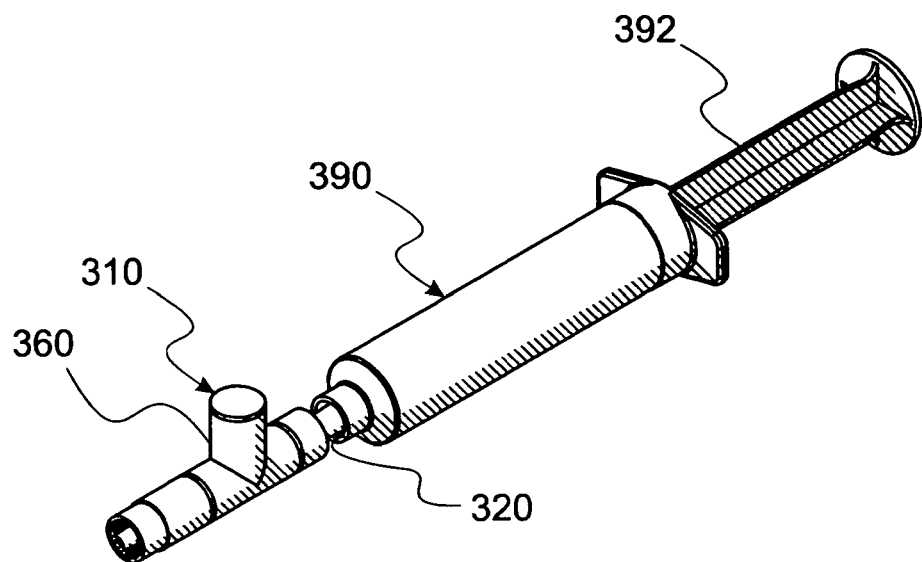
FIG. 13 is a perspective of the device seen in FIG. 9 with a syringe affixed to the device to provide a fluid pressure source.
Figure 14:
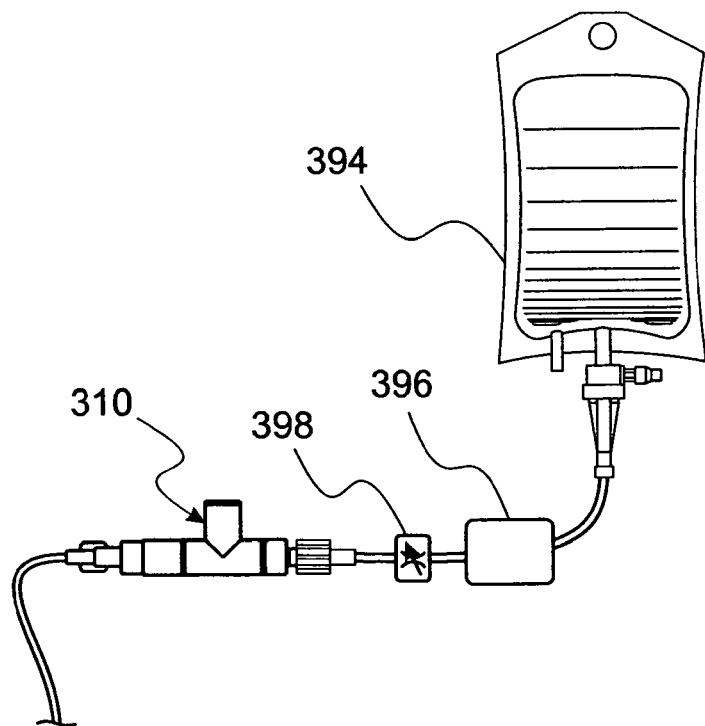
FIG. 14 is a schematic drawing of a system which employs a pumped fluid source for the device seen in FIG. 9.

Sources for pressurized fluid for device 310 are seen in FIGS. 13 and 14. In FIG. 13, a conventional syringe 390 is affixed to proximal connection 320. Source pressure is provided by the force displacing an associated plunger rod 392. Note that sufficient pressure is required to fully charge chamber 360 before actuating valve 350.

In FIG. 14, a more sophisticated pressure providing source system is seen including a saline bag 304, a pump 396 and a variable liquid flow restrictor 398. Source liquid from bag 394 is drawn and pumped by pump 396 to provide pressure equal to or greater than the high pressure necessary to open valve 350. Variable restrictor is set to determine pump 396 to device 310 liquid transfer rate to determine device 310 output pulse rate.

Figure 15:
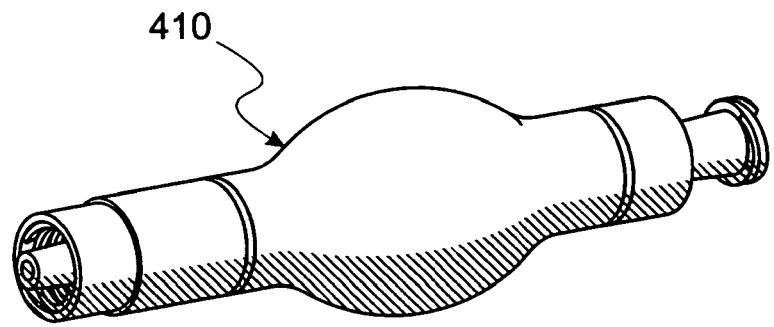
FIG. 15 is a perspective of a squeezable device for providing a controlled pressure pulse according to the instant invention.
Figure 16:
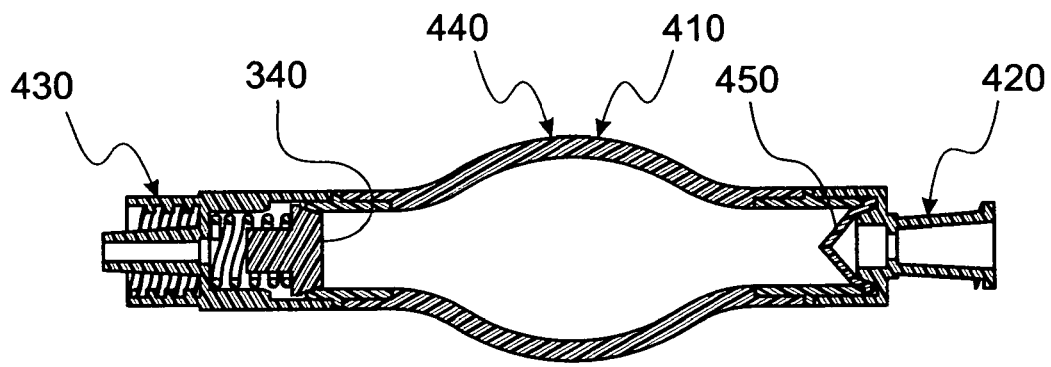
FIG. 16 is a cross section of the device seen in FIG. 15.
Figure 17:
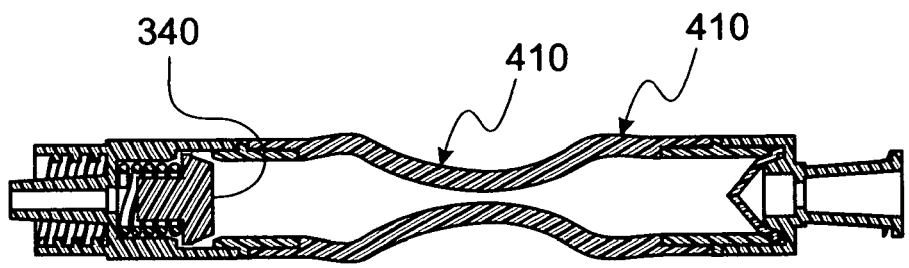
FIG. 17 is a cross section of the device seen in FIG. 14 with a medical section squeezed at the end of a controlled release pressure pulse.

Reference is now made to FIGS. 15-17 wherein an in-line pinch or squeeze pump 410, made according to the instant invention, is seen. As seen in FIG. 16, device 410 comprises an upstream or proximal connection 420, into which liquid from a liquid source is provided. Further device 410 comprises an output port and connector 430 which may be connected to a downstream catheter system. For proper operation, liquid pressure available from the source must only be greater than filling pressure of an expandable tube 440 which is sized and shaped to be easily filled and purged by squeezing.

As seen in FIG. 16, a pressure sensitive valve 340 (see also FIGS. 11-13 of device 310, disclosed supra) is disposed to close output port and connector 430 when pressure is below a predetermined pressure. Just distal from proximal connection 420 is a check valve 450 to obstruct backflow. Tube 440 provides a storage medium which defines pulse flow quantity when device 410 is actuated. To operate, tube 440 is squeezed until valve 340 is opened to provide a pressure pulse according to the present invention. Continued reflexive squeezing dispenses liquid through valve 340 to create a pulsatile flow of liquid having sufficient turbulent flow and pressure to purge an attached catheter system. Note that pressure of source liquid need only be at a sufficiently high pressure to fill tube 440 and that tube 440 may have sufficient inherent structural memory to provide a somewhat negative filling pressure requirement. This same memory reduces liquid pressure inside tube 440 to cause valve 340 to close at the end of a pulse generating cycle.

Figure 18:
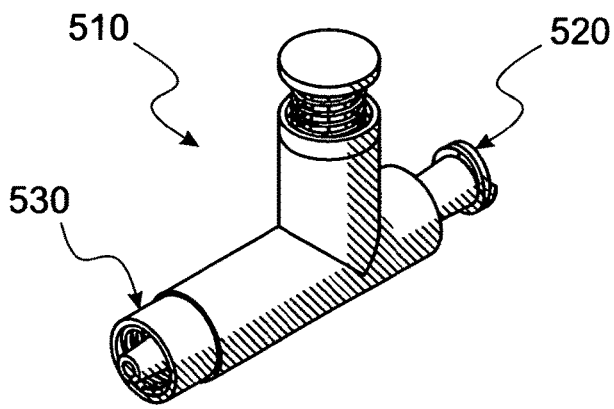
FIG. 18 is a perspective of a manually operated controlled pressure pulse device made according to the present invention.
Figure 19:
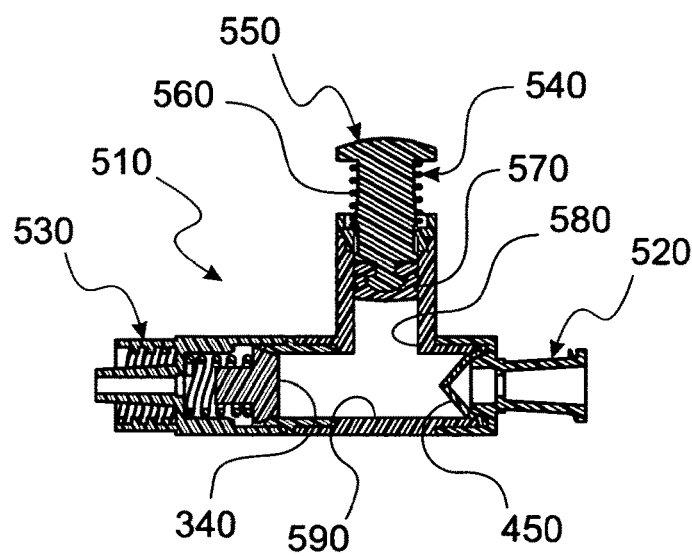
FIG. 19 is a cross section of the device seen in FIG. 18 filled before initiating a controlled pressure pulse.
Figure 20:
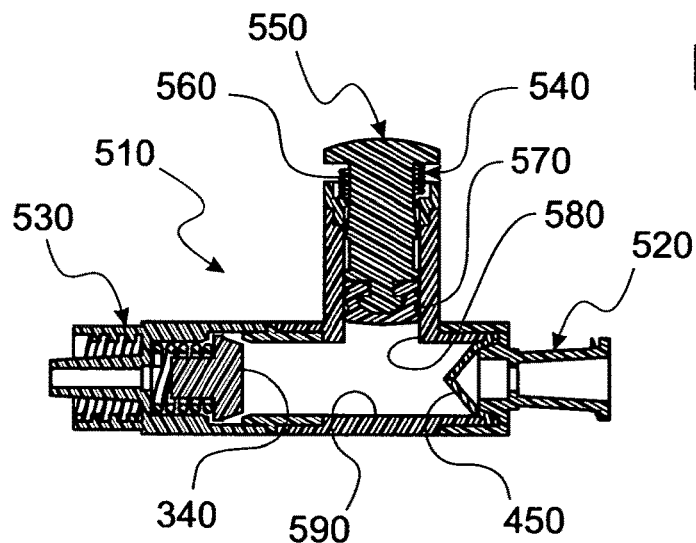
FIG. 20 is a cross section of the device seen in FIG. 18 at the end of a pressure pulse.

Another device 510 which provides manually, digitally generated controlled pressure pulses for purging catheter systems according to the present invention is seen in FIGS. 18-20. As seen in FIG. 19, device 510 comprises an upstream or proximal connection 520, into which liquid from a liquid source is provided. Further device 510 comprises an output port and connector 530 which may be connected to a downstream catheter system. For proper operation, liquid pressure available from the source must only be greater than filling pressure of a spring piston combination 540. Combination 540 comprises a depressible button and rod 550, a compressible spring 560 and a plunger 570. Plunger 570 is sized and shaped to evacuate liquid from a hollow vertical chamber 580 which communicates orthogonally with a hollow liquid flow chamber 590 disposed for liquid communication between proximal connection 520 and output port 530. Amount of liquid stored in vertical chamber 580 and released upon displacement of plunger 570 determines pulse volume of liquid delivered to the downstream catheter system.

As seen in FIG. 19, a pressure sensitive valve 340 (see also FIGS. 11-13 of device 310, disclosed supra) is disposed to close output port and connector 530 when pressure is below a predetermined pressure. Just distal from proximal connection 520 is a check valve 450 to obstruct backflow. To operate device 510, button 550 is depressed to open valve 340 thereby providing a pressure pulse according to the present invention. Continued reflexively depressing button 550 dispenses liquid through valve 340 to create a plusatile flow of liquid having sufficient turbulent flow and pressure to purge an attached catheter system. Note that pressure of source liquid need only be at a sufficiently high pressure to fill chamber 580 and that combination 540 with spring 560 should have sufficient inherent structural memory to provide a negative filling pressure inside chamber 590. This same memory reduces liquid pressure inside chamber 590 to cause valve 340 to close at the end of a pulse generating cycle.

To operate device 510, chamber 580 is permitted to fill with liquid provided through connector 520. Button 550 is depressed to provide sufficient force to open valve 340 and reflexively thereafter continued to be depressed until liquid is purged from chamber 580 as seen in FIG. 20 to produce the desired purging pressure pulse. Once combination 540 is fully depressed, force on button 550 is relieved to permit refilling of chamber 580 for generating a subsequent pressure pulse.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A flush syringe comprising:
    a barrel including a proximal opening; and
    a plunger rod disposed within the barrel for slideable displacement within the barrel, the plunger rod comprising a stem and a series of plurality of shearable actuating rings disposed along the stem;
    the plurality of shearable actuating rings obstructed by the proximal opening of the barrel;
    wherein the barrel has a proximally disposed retention ring; and
    wherein the plurality of shearable actuating rings comprises a first actuator ring and a second actuator ring, the second actuator ring proximally disposed exterior to the proximal opening of the barrel, the first actuator ring distally disposed to the second actuator ring wherein the first actuator ring is captured by the second actuator ring as the plunger rod is displaced into the barrel.

2. The flush syringe of claim 1, wherein the plurality of shearable actuating rings are sheared from the stem as the plunger rod is displaced into the barrel.

3. The flush syringe of claim 2, wherein after being sheared, the plurality of shearable actuating rings pile up at the proximal opening of the barrel and prevent full evacuation of the barrel.

4. The flush syringe of claim 1, wherein the stem of the plunger rod comprises a space between the plurality of shearable actuating rings that prevents acceleration and velocity within the barrel as the plunger rod is displaced distally within the barrel.

5. The flush syringe of claim 1, wherein displacement of the plurality of shearable actuating rings past the proximal opening of the barrel creates acceleration and velocity within the barrel.

6. The flush syringe of claim 1, wherein the barrel comprises an amount of liquid.

7. The flush syringe of claim 6, wherein the amount of liquid provides turbulent flow when the plurality of shearable actuating rings are sheared from the stem as the plunger rod is displaced into the barrel.

* * * * *